United States Patent [19]

Ario et al.

[11] Patent Number: 5,595,487
[45] Date of Patent: Jan. 21, 1997

[54] METHOD FOR BONDING AMALGAM TO DENTAL SURFACES

[75] Inventors: Paula D. Ario, Minneapolis; Steven M. Aasen, Woodbury, both of Minn.

[73] Assignee: Minnesota Mining and Manufacturing Company, St. Paul, Minn.

[21] Appl. No.: 613,950

[22] Filed: Mar. 11, 1996

Related U.S. Application Data

[63] Continuation of Ser. No. 269,157, Jun. 30, 1994, abandoned.

[51] Int. Cl.⁶ .................................. A61C 5/04; A61C 5/00
[52] U.S. Cl. ..................... 433/226; 433/217.1; 433/228.1
[58] Field of Search .................................. 433/217.1, 218, 433/219, 226, 228.1

[56] References Cited

U.S. PATENT DOCUMENTS

| | | |
|---|---|---|
| 3,513,123 | 5/1970 | Saffir . |
| 3,574,943 | 4/1971 | Stark et al. . |
| 3,882,600 | 5/1975 | Plymale . |
| 3,997,504 | 12/1976 | Playmale . |
| 4,001,483 | 1/1977 | Lee, Jr. et al. . |
| 4,064,629 | 12/1977 | Stoner et al. . |
| 4,182,035 | 1/1980 | Yamauchi et al. . |
| 4,222,780 | 9/1980 | Shibatani et al. . |
| 4,235,633 | 11/1980 | Tomioka et al. . |
| 4,259,117 | 3/1981 | Yamauchi et al. . |
| 4,368,043 | 1/1983 | Yamauchi et al. . |
| 4,383,052 | 5/1983 | Higo et al. . |
| 4,499,251 | 2/1985 | Omura et al. . |
| 4,514,342 | 4/1985 | Billington et al. . |
| 4,515,930 | 5/1985 | Omura et al. . |
| 4,535,102 | 8/1985 | Kusumoto et al. . |
| 4,537,940 | 8/1985 | Omura et al. . |
| 4,539,382 | 9/1985 | Omura et al. . |
| 4,540,722 | 9/1985 | Bunker . |
| 4,544,467 | 10/1985 | Bunker et al. . |
| 4,669,983 | 6/1987 | Bunker . |
| 4,872,936 | 10/1989 | Engelbrecht . |
| 4,929,746 | 5/1990 | Bunker . |
| 5,151,479 | 9/1992 | Mukai et al. ............... 526/277 |
| 5,171,149 | 12/1992 | Alpert ..................... 433/217.1 |
| 5,256,447 | 10/1993 | Oxman et al. . |
| 5,264,513 | 11/1993 | Ikemura et al. ............ 526/318 |
| 5,276,068 | 1/1994 | Waknine . |
| 5,302,630 | 4/1994 | Mukai et al. ............... 523/118 |

FOREIGN PATENT DOCUMENTS

| | | |
|---|---|---|
| 0058483 | 8/1982 | European Pat. Off. . |
| 0234934 | 9/1987 | European Pat. Off. . |
| 0237233 | 9/1987 | European Pat. Off. . |
| 0348718 | 1/1990 | European Pat. Off. . |
| 0408357 | 1/1991 | European Pat. Off. . |
| 0423430 | 4/1991 | European Pat. Off. . |
| 0661034 | 7/1995 | European Pat. Off. . |
| 2561521 | 9/1985 | France . |
| 2739282 | 3/1978 | Germany . |
| 57-143372 | 9/1982 | Japan . |
| 57-167364 | 10/1982 | Japan . |
| 63-175085 | 7/1988 | Japan . |
| 63-250310 | 10/1988 | Japan . |
| WO93/12758 | 7/1993 | WIPO . |

OTHER PUBLICATIONS

International Search Report.
Derwent Publication; JP 60 123 515, 2 Jul. 1985.
M. Staninec and M. Holt, *Journal of Prosthetic Dentistry* (1988), vol. 59, pp. 397–402.
A. Lacey and M. Staninec, *Quintessence International* (1989), vol. 20, pp. 521–524.
Y. Torri, et al. *Operative Dentistry* (1989), vol. 14, pp. 142–148.
CRA Newsletter; Adhesives, Silver Amalgam, (Feb. 1994).
Y. Aboush and C. Jenkins, *Br. Dent. J.* (1989), vol. 166, pp. 255–257.
Y. Aboush and R. Elderton, *Br. Dent. J.* (1991), vol. 170, pp. 219–222.
Y. Aboush and R. Elderton, *Dent. Mater.* (1991), vol. 7, pp. 130–132.
A. Ben–Amar, *J. Am. Dent. Assoc.* (1989), vol. 119, pp. 725–728.
M. Mitrosky, Jr., *Quintessence International* (1981), vol. 9, pp. 871–874.
H. J. Staehle et al., *Dtsch. Zahnartzt* (1988), vol. 43, pp. 952–957.
M. Buonocore, W. Wileman, and F. Brudevold, *J. Dent. Res.*, 35, 846 (1956).
M. Buonocore and M. Quigley, *J. Amer. Dent. Assoc.*, 57, 807 (1958).
M. Anbar and E. Farley, *J. Dent. Res.*, 53, 879 (1974).
E. Farley, R. Jones, and M. Anbar, *J. Dent. Res.*, 56, 943 (1977).

*Primary Examiner*—Nicholas D. Lucchesi
*Attorney, Agent, or Firm*—Gary L. Griswold; Walter N. Kirn; Dale A. Bjorkman

[57] ABSTRACT

A method for adhering amalgam to a dental surface comprising the steps of a) etching the dental surface with acid, b) applying a treatment composition comprising an aromatic sulfinate salt to the etched dental surface, c) applying a priming solution containing a film-former to the treated dental surface, d) applying a chemically curable dental adhesive to the primed dental surface, and e) applying amalgam to the adhesive-coated dental surface. The chemically curable adhesive comprises an oxidizing agent and a reducing agent. The oxidizing agent is present in an amount sufficient to interact with said aromatic sulfinate salt to achieve higher adhesion to the dental surface than a like method not comprising an aromatic sulfinate salt in the treatment composition.

20 Claims, No Drawings

METHOD FOR BONDING AMALGAM TO DENTAL SURFACES

This is a continuation of application Ser. No. 08/269,157 filed Jun. 30, 1994 now abandoned.

FIELD OF THE INVENTION

The present invention relates to bonding of amalgam to dental surfaces. More specifically, the present invention relates to multiple-step procedures for bonding dental amalgam to hard tissue, amalgam or other surfaces of the oral environment.

BACKGROUND OF THE INVENTION

Dental amalgam has been available to the dental profession for well over a century and it is used extensively for intracoronal and extracoronal restorations. Amalgam is highly durable and the strength and occlusal wear characteristics of alternative materials such as composite resins are generally compared to that of amalgam. However, amalgam does not adhere to tooth structure and the dentist must take great care to prepare the tooth cavity with dovetails and various cutout grooves which in effect mechanically lock the amalgam into the cavity. Such required preparation by the dentist results in the need to excavate more tooth structure than would otherwise be necessary if the amalgam were adhesive. This of course weakens the tooth. Additionally, microleakage tends to occur at the interface of the amalgam and cavity wall. Microleakage allows penetration of bacteria, soluble salts and saliva into any space between the amalgam restoration and cavity walls. This can lead to inflammation and pulp irritation which in turn can cause other complications. The penetration of bacteria into spaces between the amalgam and cavity wall can demineralize the cavity walls and lead to formation of recurrent caries. Corrosion of amalgam can cause one of the amalgam alloy metals, for example tin, to deposit along the amalgam and cavity wall interface. This usually leads to tooth discoloration along the interface and can noticeably detract from the esthetic appearance of tooth and restoration. An adhesive seal between amalgam restoration and cavity walls could prevent microleakage. An adhesive amalgam could significantly reduce the amount of tooth the dentist needs to excavate in order to prepare the cavity for restoration. An adhesive amalgam could impart significantly more strength to the filled tooth structure.

U.S. Pat. No. 3,513,123 (Saffir) discloses an epoxy liquid resin composition which is added to amalgam in an effort to make the amalgam adhere to tooth structure. This reference discloses use of an epoxy liquid resin additive consisting of a glycidyl ether type epoxy resin containing a polyamine hardening agent.

U.S. Pat. No. 4,064,629 (Stoner), discloses a method for applying amalgam restorations which involves precoating the surfaces of a cavity within a carious tooth with a layer of an "adhesive-metal" lining composition. The metal of the lining composition is amalgamated by diffusion of the mercury from the subsequently applied conventional dental amalgam filling. The "adhesive-metal" lining composition is said to improve corrosion resistance of the dental amalgam filling and also promotes bonding between the amalgam restoration and the cavity surfaces. Other references which disclose precoating the surfaces of a tooth cavity with an adhesive coating said to adhere to conventional amalgam are, for example, U.S. Pat. Nos. 4,001,483 (Lee) and 3,574,943 (Nicholson).

In recent years several adhesive products which claim to make amalgam adhere to tooth structure have been made available to dental clinicians. (The term "tooth structure" as used hereinafter shall be interpreted to include either or both dentin and enamel.) One such product is sold in a kit form under the trademark "AMALGAMBOND" available from Parkell Co. The "AMALGAMBOND" product is a liquid adhesive resin which is coated directly onto tooth structure. The curing procedure also requires use of an air-sensitive catalyst which if dropped on flammable paper causes smoldering. The active ingredients in the adhesive are 4-META (4-methacryloxyethyl trimellitic anhydride) and TBB (tri-n-butylborane). Other products which similarly involve coating a specific curable resin directly onto tooth structure to make amalgam adhere are available under the trademarks "PANAVIA" Dental Adhesive from Kuraray Company and "SUPERBOND" Adhesive from Sun Medical Co., Ltd., Kyoto, Japan.

Literature articles which disclose bonding of amalgam to tooth structure by precoating the tooth with adhesive resin include M. Staninec and M. Holt, *Journal of Prosthetic Dentistry* (1988), Vol. 59, p. 397–402, A. Lacey and M. Staninec, *Quintessence International* (1989), Vol. 20, p. 521–524, and Y. Torii, et al. *Operative Dentistry* (1989), Vol. 14, p. 142–148. The above listed articles report improved adhesive tensile strength between amalgam and coated tooth structure but do not report adhesive shear bond strength of the amalgam.

U.S. Pat. No. 5,276,068 to Waknine discloses dental compositions useful for bonding dental surfaces, including enamel, dentin, porcelain and metallic surfaces, comprising polycarbonate dimethacrylate condensation products as a principle component, and a secondary monomer such as BIS-GMA or urethane dimethacrylate or the like as a second component, which is provided to impart strength to the dental composition. Also described therein are methods for bonding dental restorative materials to an exposed dentin surface, wherein the surface can be pretreated by application of 3% $H_2O_2$, 17% EDTA, or 5% NaOCl in non-vital teeth followed by an alcohol or acetone solution of an alkali metal salt of benzenesulfinic acid with subsequent evaporation of the alcohol from the solution. Alternatively, the surface can be pretreated by first applying an alcohol or acetone solution of an alkali metal salt of benzenesulfinic acid and then applying an acetone solution of N-phenylglycine. The treated dentin surface is then coated with a resinous adhesive. The adhesive is then cured and an appropriate dental restorative material is applied.

SUMMARY OF THE INVENTION

The present invention provides a method for adhering amalgam to a dental surface comprising the steps of a) etching the dental surface with acid; b) applying a treatment composition comprising an aromatic sulfinate salt to the etched dental surface, c) applying a priming solution containing a film-former to the treated dental surface; d) applying a chemically curable dental adhesive to the primed dental surface, said chemically curable adhesive comprising oxidizing agent and a reducing agent, said oxidizing agent being present in an amount sufficient to interact with said aromatic sulfinate salt to achieve higher adhesion to the dental surface than a like method not comprising an aromatic sulfinate salt in the treatment composition; and e) applying amalgam to the adhesive-coated dental surface.

DETAILED DESCRIPTION

The present invention offers distinct advantages to the dental patient for receiving comparatively low cost and low trauma dental care. Dentists are currently extremely comfortable with the use of amalgam to restore lost tooth structure. With the present method of bonding amalgam to various dental surfaces, the dentist can perform repairs using a low cost material with which he or she is familiar. These repairs can now be made with substantially less dental surface preparation than required previously. Because the amalgam adheres to the tooth structure (including both dentin and enamel) using the present method, the dentist generally will not need to excavate as much tooth structure in preparing the cavity as would be necessary when placing a conventional amalgam restoration. This results in a saving of tooth structure and reduces the chance of the tooth weakening because of the cavity preparation. Also, the present invention significantly reduces the chance of microleakage occurring at the interface between the amalgam and cavity walls, since the adhesive bond between amalgam and tooth structure discourages penetration of bacteria, soluble salts and saliva between the amalgam restoration and cavity walls.

Additionally, the present method allows bonding of the amalgam to other dental surfaces that previously could not be repaired using amalgam without complete removal of prior dental work. The present method bonds amalgam to previously placed amalgam, metal (such as in pins, posts and bridgework), porcelain, previously placed composite restorations or other materials used in the oral environment.

Generally, before the present method is carried out, the area of the oral cavity to be worked on is prepared using conventional dental techniques. For example, hard tissue (e.g. enamel or dentin) to which the amalgam is to be applied preferably is first cleaned using conventional methods (e.g., by abrading it with a bur), rinsed (e.g., using water) and dried (e.g., using air).

In the first step of the present method, the dental surface is etched with acid. Any appropriate acid etch technique may be used to provide a surface receptive to bonding materials thereto.

Acids for use in the acid etch step can be inorganic or organic acids, and if organic can be monomeric, oligomeric or polymeric. If desired, a precursor to the acid such as an acid anhydride, e.g., 4-Methacryloxyethyl Trimellitate Anhydride (4-META), acid halide (including inorganic acid halides such as Lewis acids, e.g., ferric chloride, and organic acid halides), or ester can be used in place of the acid itself, e.g., to generate the desired acid in situ. Suitable acids include mineral acids, carboxylic acids, sulfonic acids, and phenols, with carboxylic acids, alkylsulfonic acids, arylsulfonic acids, and phosphonic acids being preferred.

The acid has a pKa in water that is less than or equal to that of phenol. Preferably, the pKa of the acid is between about −20 and about +10, more preferably between about −10 and about +5.

Suitable inorganic acids include HBr, HCl, and $HNO_3$. Suitable organic acids include acetic acid, ∝-chloropropionic acid, 2-acrylamido-2-methylpropane sulfonic acid, acrylic acid, benzenesulfonic acid, benzoic acid, bromoacetic acid, 10-camphorquinone-sulfonic acid, 10-camphorsulfonic acid, chloroacetic acid, citraconic acid, citric acid, dibromoacetic acid, dichloroacetic acid, di-HEMA ester of 1,2,4,5 benzenetetracarboxylic acid, 2,4-dinitrophenol, formic acid, fumaric acid, 2-hydroxy-4-methoxybenzophenone-5-sulfonic acid, maleic acid, methacrylic acid, 2-naphthalene sulfonic acid, nitric acid, oxalic acid, p-nitrophenol, phenol, phosphoric acid, phosphorous acid esters (such as 2,2'-bis(∝-methacryloxy-β-hydroxypropoxyphenyl) propane diphosphonate (Bis-GMA diphosphonate), dibutyl phosphite, di-2-ethylhexyl phosphate, di-2-ethylhexyl phosphite, hydroxyethyl methacrylate monophosphate, glyceryl dimethacrylate phosphate, glyceryl-2-phosphate, glycerylphosphoric acid, methacryloxyethyl phosphate, pentaerythritol triacrylate monophosphate, pentaerythritol trimethacrylate monophosphate, dipentaerythritol pentaacrylate monophosphate, and dipentaerythritol pentamethacrylate monophosphate), pivalic acid, propionic acid, sulfuric acid, toluene sulfonic acid, tribromoacetic acid, trichloroacetic acid, trifluoroacetic acid, trifluoromethanesulfonic acid, and trihydroxybenzoic acid. Mixtures of such acids can be used if desired.

Where the dental surface to be bonded to is dentin, preferably the acid does not generate insoluble salts of calcium during the etch technique in an amount that would detrimentally affect adhesion to the oral surface. If the acid does generate insoluble calcium salts, the salts are preferably rinsed from the dental surface before subsequent steps are taken.

Under typical conditions, the dental surface to be bonded is first exposed to about 0.01–0.2 ml of acid solution for a period of about 5–60 seconds. Preferred etching solutions contain about 10% maleic acid or about 35% phosphoric acid. Generally, the higher the acid strength and concentration, the shorter the time of exposure to the acid solution required to achieve the desired effect. This acid may be applied with dropper sponge or brush. The acid solution may optionally be dried on the dental surface by, e.g. air.

After the dental surface is etched with acid, a treatment composition comprising an aromatic sulfinate salt is applied to the etched dental surface. The preferred aromatic sulfinate salt is represented by the general formula

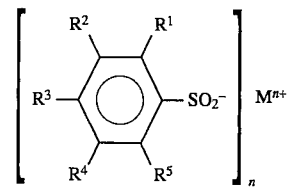

In the above-mentioned general formula, $R^1$, $R^2$, $R^3$, $R^4$ and $R^5$ may be any atoms and/or groups as long as they are inert to the double bond of monomers. Examples are hydrogen, fluoro, chloro, bromo, iodo, methyl, ethyl, 2-chloroethyl, 2-bromo-2-chloroethyl, propyl, isopropyl, per-fluoropropyl, allyl, butyl, isobutyl, sec-butyl, tert-butyl, pentyl, isopentyl, neopentyl, tertpentyl, cyclohexyl, phenyl and 4-bromophenyl.

$M^{n+}$ is a cation with mono-valency to 4-valency that can, as a counter ion for sulfinic acid anion, form the sulfinate. Examples of $M^{n+}$ are alkali metal ions, such as $Li^+$, $Na^+$, $K^+$, $Rb^+$, and $Cs^+$, alkaline earth metal ions, such as $Be^{2+}$, $Mg^{2+}$, $Ca^{2+}$, $Sr^{2+}$ and $Ba^{2+}$, transition metal ions such as $Cr^2$, $Cr^{3+}$, $Mn^{2+}$, $Fe^{2+}$, $Fe^{3+}$, $Co^{2+}$, $Co^{3+}$, $Ni^{2+}$, $Cu^{2+}$, $Zn^{2+}$, $Rh^{3+}$, $Pd^{2+}$, $Ag^{30}$, $Cd^{2+}$, $Ir^{3+}$, $Ir^{4+}$, and $Hg^{2+}$, and ammonium ions, such as $NH_4^+$, $(CH_3CH_2)_3NH^+$,

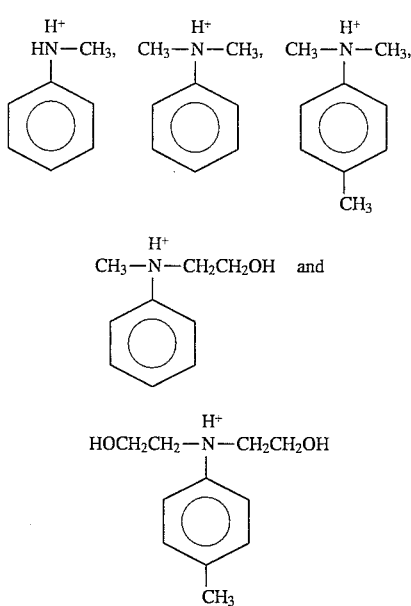

Preferred counter ions among these ions are Li$^+$, Na$^+$, K$^+$, Mg$^{2+}$, and Ca$^{2+}$, since sulfinates thereof have good stability when stored in monomers and have good solubility in the monomers.

Particularly preferred aromatic sulfinate salts include sodium benzenesulfinate and sodium toluenesulfinate. Optionally, the treatment composition may comprise mixtures of more than one aromatic sulfinate salt.

The aromatic sufinate salt is preferably provided in an appropriate solvent, such as water, acetone, lower alkyl alcohols (such as methanol, ethanol, propanol) and the like.

Optionally the treatment composition containing the aromatic sulfinate salt may comprise other adjuvants, such as polymerization catalysts, medicaments, fluoride compounds, indicators, dyes, wetting agents, buffering agents, thixotropes and the like.

The treatment composition preferably comprises at least 0.1% by weight of aromatic sulfinate salt, more preferably between 0.5 and 15%, and most preferably between one and 10%. The treatment composition may be applied by any appropriate means, such as by dropper, sponge or brush. This composition is preferably allowed to reside on the etched surface for about 1–60 seconds.

The treatment composition is optionally dried on the surface with air, or the solvent is allowed to evaporate. After the treatment composition comprising an aromatic sulfinate salt is applied to the etched dental surface, a priming solution containing a film-former is applied to the treated dental surface. For purposes of the present invention, a film-former is defined as a composition capable of forming a hardenable (e.g., polymerizable) continuous or semicontinuous film on the dental surface.

The film-former used in the primer of the present invention is preferably a water-dispersible substance or water-dispersible mixture of substances, such substance(s) being organic monomers, oligomers, polymers, or cosolvents. Most preferably, the film-former contains at least one polymer prior to application to the treated dental surface. As used herein, a "water-dispersible" film-former has a water dispersibility or more preferably a water solubility (exclusive of any water that may be present in the film-former) of at least about 5 weight percent. Most preferably, the film-former can be mixed with water in all proportions. For brevity, dispersible and soluble will sometimes be referred to collectively as dispersible. As used herein, "solubility" means the capability of a substance to form a solution, i.e., either a true solution or a colloidal solution. A true solution being a uniformly dispersed mixture at the molecular or ionic level, of one or more substances (the solute) in one or more substances (the solvent). These two parts of a solution are called phases. A colloidal dispersion is often called a solution. Since colloidal particles are larger than molecules it is strictly incorrect to call such dispersions solutions; however this term is widely used in the literature. As used herein, "dispersibility" means the capability of a substance to form a dispersion, i.e., a two-phase system where one phase consists of finely divided particles (often in the colloidal size range) distributed throughout a bulk substance, the particles being the disperse or internal phase and the bulk substance the continuous or external phase.

Preferred film-formers contain one or more substances having a sufficient number of water-dispersing groups such as hydroxyl groups, carboxyl groups, sulfonic acid groups, cationic salts (e.g., ammonium, phosphonium or sulfonium groups), amide linkages or polyether linkages to render the film-former water-dispersible. The film-former, prior to removal of any volatile components, preferably wets the dental surface and most preferably has a sufficiently low viscosity to enable it to flow into interstices that already exist in the dental surface or that are created therein by the action of the acid. After removal of any volatile components, the film-former preferably has a sufficiently high viscosity to enable it to resist displacement by dentinal fluids (in the case where the dental surface is dentin) or other extraneous liquids. The film-former preferably contains one or more polymerizable substances. Addition polymerizable substances (e.g., vinyl compounds such as acrylates and methacrylates) are especially preferred.

Suitable preferred polymer components in the fihn-former include linear, branched or cyclic polymers formed prior to priming of the treated dental surface. For purposes of this invention, a polymer is a chemical compound having at least two repeat units. They can be polymers of ethylenically unsaturated monomers or they can be polymeric compounds like polyester, polyamide, polyether, polyethyleneglycol, polyethyleneglycol dimethacrylate and diacrylate, polysaccharide, cellulosic, polypropylene, polyacrylonitrile, polyurethane, poly(vinyl chloride), poly(methyl methacrylate), phenol-formaldehyde, melamine-formaldehyde, and urea-formaldehyde. Mixtures of such polymers can be used if desired.

Preferred polymers are the polymers of ethylenically unsaturated monomers. These polymers may be homo- or co-polymers and may contain hydrophilic or hydrophobic groups. The polymer may optionally contain acid groups, their salts, or their reactive derivative groups. Particularly preferred polymers contain reactive groups that further react (i.e., crosslink or copolymerize) with the other components of the film-former or the dental adhesive. Addition polymerizable reactive groups (e.g., vinyl groups such as acrylates and methacrylates) are especially preferred. Polymers of ethylenically unsaturated monomers are often used in dental glass ionomer cements. These polymers are especially useful in the present invention as they generally have good biocompatibility, are dispersible in water and have a suitable molecular weight. Particularly preferred polymers contain functional groups that have an affinity for hard tissue. For example, such groups include β-dicarbonyl groups and carboxylic acid groups. The polymer component of an ionomer cement is often a copolymer of acrylic acid and itaconic acid, although other monomers may be incorporated, and are herein referred to as polyalkenoic acids. See generally, Prosser et al., *Developments in Ionic Polymers—1*, Chapter 5, Applied Science Publishers (London and New York, 1983). Recently such polymers have been further modified in the laboratory of the assignee of this invention by the incorporation of addition polymerizable reactive groups as mentioned above. Their preparation is described in U.S. Pat. No. 5,130,347.

Preferred polymeric compounds used in the primer of the invention have a weight average molecular weight prior to hardening of more than about 500, although preferably no greater than 2,000,000. More preferably, polymeric compounds for use in the primer have a weight average molecular weight prior to hardening of between about 1,000 and 1,000,000 evaluated against a polystyrene standard using gel permeation chromatography. Most preferably, polymeric compounds for use in the primer have a weight average molecular weight prior to hardening of between about 5,000 and 200,000.

Suitable monomer components in the film-former include 2-hydroxyethylacrylate, 2-hydroxyethylmethacrylate ("HEMA"), 2- and 3-hydroxypropylacrylate and methacrylate, 1,3- and 2,3-dihydroxypropylacrylate and methacrylate, 2-hydroxypropyl-1,3-diacrylate and dimethacrylate, 3-hydroxypropyl-1,2-diacrylate and dimethylacrylate, pentaerythritol diacrylate and dimethacrylate, acrylic acid, methacrylic acid, 2-trimethylammonium ethylmethacrylic chloride, 2-acrylamido-2-methylpropane-sulfonic acid, acrylamide, methacrylamide, 2-hydroxyethylacrylamide and methacrylamide, N,N-bis(2-hydroxyethyl)acrylamide and methacrylamide, N-alkyl-N-hydroxyethyl acrylamides and methacrylamides, 2- and 3-hydroxypropylacrylamide and methacrylamide, methacrylamidopropyltrimethylammonium chloride, polyethyleneglycol (400) diacrylate and dimethacrylate, glycerol dimethacrylate and diacrylate, gylcerol monomethacrylate and monoacrylate, pentaerylthritol trimethacrylate and triacrylate, and mixtures thereof. It is expected that where an acrylate monomer is suitable the methacrylate analog will likewise be suitable.

Alternatively, water insoluble or sparingly water soluble components may also be incorporated in useful primers of the present invention. For example tetraethylene glycol dimethacrylate ("TEGDMA"), a sparingly water soluble monomer, may provide excellent priming action. Additionally, some amount of water insoluble components, such as the dimethacrylate derived from the reaction between methacrylic acid and the diglycidyl ether of bisphenol A ("Bis-GMA") may also be incorporated in the present primers with good overall bonding results.

The film-former preferably comprises one or more suitable cosolvents. The cosolvent(s) aid in wetting the dental surface (especially when the surface is hard tissue) and in solubilizing or dispersing the substances. Suitable cosolvents include water, alcohols such as methanol, ethanol, 1-propanol, 2-propanol, and 2-methyl-2-propanol, ketones such as acetone and methylethylketone, aldehydes such as formaldehyde, acetaldehyde, propionaldehyde, acrolein, glutaraldehyde and 2-hydroxy-adipaldehyde, amides such as acetamide and N,N-dimethylformamide, and other substances such as tetrahydrofuran and dimethyl sulfoxide. The film-former preferably contains less than about 95 weight percent cosolvent, more preferably between about 15 and about 85 weight percent cosolvent.

The primer preferably also is acidic. Acidity may be provided by incorporating an acid or acid precursor in the priming solution, or by providing the film-former with acidic functionality. Preferably, the priming solution has a pH of less than 7.

When the acidity of the primer is provided through incorporation of a separate acid, the acid may preferably be selected from the same acids recited above for use in the acid etch step.

The above discussion on selection of film-former components identifies a number of materials that contain acidic functionality. It will be appreciated by the skilled artisan that selection of these acid functional film-formers is preferred for imparting acidity to the primer solution.

The priming solution may optionally contain other adjuvants such as polymerization catalysts, medicaments, fluoride compounds, indicators, dyes, wetting agents, buffering agents, thixotropes and the like.

The priming solution is applied by appropriate means, such as a dropper, sponge or brush, and should be allowed to stand on the dental surface long enough to provide the desired degree of priming. The standing time will depend upon the film-former employed, the type of dental surface and the time available for carrying out the priming procedure. For priming dentin and enamel, standing times less than about 5 minutes, and preferably about one second to one minute provide very effective priming, although shorter or longer times can be used if desired.

The priming solution is optionally hardened on the dental surface before subsequent steps are taken. Hardening may be achieved by allowing the priming solution to dry, or optionally polymerizing the film-former. In order to initiate the polymerization reaction, the film-former may comprise polymerization catalysts such as those mentioned in columns 28 and 29 of U.S. Pat. No. 4,539,382 and described in more detail below.

Alternatively, the priming solution may contain one or more suitable photopolymerization initiators that act as a source of free radicals when activated. Such initiators can be used alone or in combination with one or more accelerators and/or sensitizers.

The photoinitiator should be capable of promoting free radical crosslinking of the ethylenically unsaturated moiety on exposure to light of a suitable wavelength and intensity. Visible light photoinitiators are preferred. The photoinitiator frequently can be used alone, but typically it is used in combination with a suitable donor compound or a suitable accelerator (for example, amines, peroxides, phosphorus compounds, ketones and alpha-diketone compounds).

Preferred visible light-induced initiators include camphorquinone (which typically is combined with a suitable hydrogen donor such as an amine), diaryliodonium simple or metal complex salts, chromophore-substituted halomethyl-s-triazines and halomethyl oxadiazoles. Particularly preferred visible light-induced photoinitiators include combinations of an alpha-diketone, e.g., camphorquinone, and a diaryliodonium salt, e.g., diphenyliodonium chloride, bromide, iodide, or hexafluorophosphate, with or without additional hydrogen donors (such as sodium benzenesulfinate, amines and amine alcohols).

Preferred ultraviolet light-induced polymerization initiators include ketones such as benzyl and benzoin, and acyloins and acyloin ethers. Preferred commercially available ultraviolet light-induced polymerization initiators include 2,2-dimethoxy-2-phenylacetophenone ("IRGACURE 651") and benzoin methyl ether (2-methoxy-2-phenylacetophenone), both from Ciba-Geigy Corp.

The photoinitiator should be present in an amount sufficient to provide the desired rate of photopolymerization.

This amount will be dependent in part on the light source, the thickness of the layer to be exposed to radiant energy, and the extinction coefficient of the photoinitiator. Typically, the photoinitiator components will be present at a total weight of about 0.01 to about 5%, more preferably from about 0.1 to about 5%, based on the total weight of the composition.

After the priming solution is applied to the treated dental surface, a chemically curable dental adhesive is applied to the primed dental surface.

The chemically curable dental adhesive comprises polymerizable components in a formulation that, upon application to the surface to be bonded, initiates a cure reaction that will result in polymerization of the adhesive and bonding of amalgam to the dental surface. This cure reaction takes place without the need to expose the chemically curable dental adhesive to actinic light. Optionally, however, the dental adhesive may additionally contain photoinitiators as described above to assist in curing the adhesive at exposed margins of the amalgam placement. Generally, chemically curable dental adhesives are provided in a two part format wherein one part contains one part of a reactive pair, and the other part the other half of the pair. Optionally, the chemically curable dental adhesive may be provided in a one part formulation or three or more part formulation. Upon mixing, these components react, initiating a polymerization reaction.

The chemically curable adhesive comprises an oxidizing agent and a reducing agent. The oxidizing agent is present in an amount sufficient to interact with the aromatic sulfinate salt to achieve higher adhesion to the dental surface than a like method not comprising an aromatic sulfinate salt in the treatment composition. Various redox systems are described in U.S. Pat. No. 5,154,762, the disclosure of which is expressly incorporated herein by reference.

The oxidizing agent should react with or otherwise cooperate with the reducing agent to produce free radicals capable of initiating polymerization of the ethylenically unsaturated moiety. The oxidizing agent and the reducing agent preferably are sufficiently shelf stable to permit their storage and use under typical dental conditions. The oxidizing agent and the reducing agent should also be present in an amount sufficient to permit an adequate free radical reaction rate. This can be evaluated by combining the ethylenically unsaturated moiety, the oxidizing agent and the reducing agent and observing whether or not a hardened mass is obtained.

Suitable oxidizing agents include persulfates such as sodium, potassium, ammonium and alkyl ammonium persulfates, benzoyl peroxide, hydroperoxides such as cumene hydroperoxide, tert-butyl hydroperoxide, tert-amyl hydroperoxide and 2,5-dihydroperoxy-2,5-dimethylhexane, salts of cobalt (III) and iron (III), hydroxylamine, perboric acid and its salts, salts of a permanganate anion, and combinations thereof. Hydrogen peroxide can also be used, although it may, in some instances, interfere with the photoinitiator, if one is present. The oxidizing agent may optionally be provided in an encapsulated form as described in U.S. Pat. No. 5,154,762.

Preferred reducing agents include ascorbic acid, metal complexed ascorbic acid, cobalt (II) chloride, ferrous chloride, ferrous sulfate, hydrazinc, hydroxylamine, oxalic acid, thiourea, tertiary aromatic amines (such as N,N-bis-(2-hydroxyethyl)-p-toluidine, 4-(dimethylamino)phenethyl alcohol and the like), and aromatic salts of a dithionite, thiosulfate, benzenesulfinate, or sulfite anion.

A specifically preferred redox system for use in the chemically curable dental adhesive comprises benzoyl peroxide as an oxidizing agent and N,N-bis-(2-hydroxyethyl)-p-toluidine as a reducing agent. More preferably, the chemically curable dental adhesive contains at least about 0.75 weight percent of benzoyl peroxide and N,N-bis-(2-hydroxyethyl)-p-toluidine combined, and the ratio of weight percentages of N,N-bis-(2-hydroxyethyl)-p-toluidine to benzoyl peroxide is greater than 0.05 but less than 1.50. Most preferably, the chemically curable dental adhesive contains at least about 1 weight percent of benzoyl peroxide and N,N-bis-(2-hydroxyethyl)-p-toluidine combined, and the ratio of weight percentages of N,N-bis-(2-hydroxyethyl)-p-toluidine to benzoyl peroxide is greater than 0.10 but less than 1.20. For example, a preferred curable dental adhesive would comprise 0.75% by weight of an oxidizing agent based on total weight of the curable dental adhesive, and 0.25% by weight of a reducing agent based on total weight of the curable dental adhesive. The ratio of these weight percentages is 0.25%/0.75%=0.3.

A preferred dental adhesive is obtained by combining (1) Bis-GMA with (2) a hydrophilic monomer such as HEMA, hydroxypropyl methacrylate, or methacrylic acid. Suitable monomers for use in the dental adhesive include the monomers described above as well as tetrahydrofurfuryl methacrylate, glyceryl-1,3-dimethacrylate, triethyleneglycol dimethacrylate, ethyl methacrylate, n-hexyl methacrylate, polyethyleneglycol dimethacrylate ("PEGDMA"), and 1,6-hexanediol dimethacrylate. Optionally, the dental adhesive may contain polymers of the type described in the discussion of the priming solution above. The dental adhesive can also contain cosolvents of the type described above. Preferably the dental adhesive is copolymerizable with the residual film formed by the primer. If desired, the dental adhesive can contain conventional fillers, and can also contain adjuvants of the type described above.

Other preferred dental adhesives which can be employed with the present invention contain acrylate- or methacrylate-functional polymers and may also contain phosphorous compounds. In such dental adhesives either a single phosphorus compound or a mixture of phosphorus compounds can be used.

If desired, other free-radically polymerizable non-phosphorus-containing compounds can be mixed with the dental adhesive, for example, as a diluent to reduce viscosity or promote wetting. Other suitable free-radically polymerizable compounds include mono- or poly- (e.g., di-, tri- or tetra-functional) acrylates and methacrylates such as methyl acrylate, 2-hydroxyethyl acrylate, triethyleneglycol diacrylate, neopentylglycol diacrylate, hexamethyleneglycol diacrylate, tri methylolpropane triacrylate, pentaerythritol tetraacrylate, polyalkylene glycol mono- and di-acrylates, urethane mono- or poly-functional acrylates, Bisphenol A diacrylates, and the corresponding methacrylates of the above compounds, as well as acrylamides and methacrylamides, vinyl compounds, styrene compounds, and other olefinically unsaturated compounds suitable for use in the oral environment. U.S. Pat. Nos. 4,499,251, 4,515,930, 4,537,940 and 4,539,382 contain an extensive list of such compounds.

In use, an adhesive is applied to the primed dental surface after initiation of the polymerization reaction in an amount effective to bond the amalgam to the dental surface. After the chemically curable dental adhesive is applied to the primed dental surface, amalgam is applied to the adhesive-coated dental surface. The amalgam is prepared in the conventional manner for packing in the area for placement and applied to the adhesive coated surface before the dental adhesive is fully cured. Typically the dental practitioner has sufficient working time after application of a redox curable dental adhesive in which to place the amalgam before full curing of the adhesive. This working time varies depending on the redox curable dental adhesive used.

Amalgam preparations are typically available in capsules which contain amalgam alloy powder and mercury, sealed by a penetrable bladder located at one end of the capsule. A small rod may be included in the capsule. The clinician prepares amalgam by placing the capsule containing the alloy powder and mercury into an amalgamator. If a rod is not included the capsule may need to have the bladder mechanically broken. The amalgamator, (or triturator as it is often called), vibrates at high speed so that the rod within the capsule can penetrate the bladder to release the mercury contained therein. As mercury admixes into the alloy powder a reaction occurs between alloy powder and mercury and the amalgam slowly begins to set. At this stage the amalgam is ready for packing into the tooth cavity.

Conventional alloy powders are typically mixtures of silver, tin, copper, and zinc. Conventional amalgam alloy powders have proper proportioning of these metals to result in an alloy described in the art as a "balanced alloy." For example it is known that increasing the silver content increases the expansion of the setting amalgam, shortens setting time, increases compressive strength, and tends to make the alloy mixture more difficult to amalgamate. Tin behaves in an opposite way for all these properties. Copper and zinc contribute properties similar to silver with respect to expansion, setting time and strength, but copper is used principally for increased strength and zinc for increased resistance to tarnish. Conventional alloys are broadly classified as low-copper alloys (5% or less copper) and high copper alloys (13% to 30% copper). Commercially available low copper amalgam alloys contain typically the following compositions which apply to lathe-cut or spherical particle shapes: silver (63–70%), tin (26–28%), copper (2–5%), and zinc (0–2%). Commercially available high copper alloys are classified as admixed or unicompositional. Admixed alloys contain 33 to 60% spherical particles having a composition close to the eutectic composition of $Ag_3Cu_2$ and the balance being irregular particles. The uncompositional alloys, such as admixed alloys, have higher copper contents than the conventional lathe-cut or spherical low-copper alloys but all the particles are spherical. Commercially available high copper admixed alloys using lathe and spherical particles contain typically the following compositions: silver (40–70%), tin (0–30%), copper (2–40%), zinc (0–2%), and palladium (0–1%). Commercially available high copper unicompositional alloys use spherical typically with the following composition: silver (40–60%), tin (22–30%), copper (13–30%) inidium (0–5%) and palladium (0–1%). Mercury typically represents 40 to 60 percent by weight of the amalgam mix. A widely used high copper admixed amalgam alloy is available under the trademark "DISPERSALLOY" alloy from L.D. Caulk division of Dentsply International, Inc. The "DISPERSALLOY" alloy contains about 13% copper and the mixed "DISPERSALLOY" amalgam contains about 50% mercury. Tytin is a widely used high copper unicompositional amalgam available from Kerr Manufacturing Company, Inc.

It has been found that spherical amalgams placed using the method of the present invention exhibit superior bond strengths as compared to admixed particle amalgams.

SHEAR ADHESIVE STRENGTH TEST METHOD

Shear adhesion to dentin or enamel was evaluated as follows:

First, teeth (five bovine teeth unless otherwise noted) of similar age and appearance were partially embedded in circular acrylic discs. The exposed portion of each tooth was ground flat and parallel to the acrylic disc using Grade 120 silicon carbide paper-backed abrasive mounted on a lapidary wheel, in order to expose the dentin or enamel. During this and subsequent grinding and polishing steps, the teeth were continuously rinsed with water. Further grinding and polishing of the teeth was carried out by mounting Grade 320 silicon carbide paper-backed abrasive and then Grade 600 silicon carbide paper-backed abrasive on the lapidary wheel. The polished teeth were stored in distilled water, and used for testing within 2 hours after polishing. The polished teeth were removed from the water and dried using a stream of compressed air.

Previously prepared molds made from approximately 2-mm thick "Teflon" sheet with a hole with a 5 mm diameter gelatin capsule sleeve were clamped to each prepared tooth so that the central axis of the hole in the mold was normal to the tooth surface. The hole in each mold was filled with amalgam. It is believed that the choice of amalgam might affect the bond strength values obtained for a given adhesive system. For example, some adhesive systems of the present invention provide very strong bonds to hard tissue that are believed to fail at the amalgam-adhesive interface or within the amalgam and not at the adhesive-hard tissue interface. A higher strength amalgam may increase the measured bond strength for these adhesive systems. Therefore, comparisons between different adhesive systems should be made, wherever possible, using similar amalgam systems. The teeth and molds were allowed to stand for about 5 minutes at room temperature, then stored in distilled water at 37° C. for 24 hours unless otherwise noted. The molds were then carefully removed from the teeth, leaving a molded button of amalgam attached to each tooth.

Shear adhesive strength was evaluated by mounting the acrylic disk in a holder clamped in the jaws of an "Instron" apparatus with the polished tooth surface oriented parallel to the direction of pull. A loop of wire (0.44 mm diameter) was placed around the amalgam button adjacent to the polished tooth surface. The ends of the orthodontic wire were clamped in the pulling jaw of the Instron apparatus, thereby placing the bond in shear stress. The bond was stressed until it (or the dentin or button) failed, using a crosshead speed of 2 mm/min.

Shear adhesion to materials other than teeth was evaluated as follows:

First, the substrate to be tested (e.g.., metals, porcelain, set amalgam; ten samples unless otherwise noted) were partially embedded in circular acrylic discs. The exposed portion of each metal and set amalgam sample was polished flat and parallel to the acrylic disc using Grade 600 silicon carbide paper-backed abrasive mounted on a lapidary wheel, in order to obtain a shiny metal or amalgam surface. During these polishing steps, the metal or amalgam surface was continuously rinsed with water. The polished metal or amalgam was removed from the water and dried using a stream of water-free and oil-free compressed air. The polished and dried metal or amalgam surface was sandblasted with aluminum oxide having an average particle size of 50 microns until the metal or set amalgam surface had a uniform aluminum oxide surface. For a 5 mm diameter cross-section, this takes about 15 seconds. The sandblasted metal or amalgam was then sonicated in water for 5 minutes so loose alumina was removed. The samples were then removed from the water and dried using an oil-free and water-free stream of compressed air.

Amalgam buttons were prepared and shear adhesion performed as described for evaluation of adhesion to dentin or enamel.

The following examples are offered to aid in understanding of the present invention and are not to be construed as limiting the scope thereof. Unless otherwise indicated, all parts and percentages are by weight. The Copolymer used in these examples, unless otherwise noted, is an ethylenically unsaturated acidic copolymer prepared like the precipitated dry polymer of EXAMPLE 11 of U.S. Pat. No. 5,130,347. The adhesive used in all examples was a two part curable adhesive, wherein one part contained 0.25% CPQ, 0.38% DEHEPT, 0.50% EDMAB, 61,79% BisGMA and 37.08% HEMA. The second part contained 2.1% BPO, 0.093% BHT, 61.13% BisGMA and 36.68% HEMA. Where commercially available products were tested, manufacturer's instructions were followed.

EXPERIMENTAL

EXAMPLE 1

The effect of the selection of etchants in the present system was evaluated for bonding of Disperalloy™ amalgam to dentin following the shear adhesion strength protocol as defined above. Various etchants were used in combination with a standard treatment composition, which was three percent sodium benzenesulfinate in ethanol, and a standard primer, which was 13.3% Copolymer/39.8% HEMA/46.9% water. Bond strengths are reported in Table I.

TABLE I

| ETCHANT | SHEAR ADHESIVE BOND STRENGTH (kg/cm$^2$) |
|---|---|
| 10% maleic acid with H$_2$O rinse | 48 ± 23 |
| 10% maleic acid - no rinse | 60 ± 14 |
| 35% phosphoric acid with H$_2$O rinse | 79 ± 19 |
| No etch | 7 ± 15 |
| 35% phosphoric acid - no rinse | 0 |

This example shows that significant improvement of bonding of amalgam to dentin was provided by using an acid etch technique where no insoluble salts were allowed to remain on the surface of the dentin.

EXAMPLE 2

The effect of the selection of components incorporated in the treatment composition for adhesion of amalgam to dentin was evaluated with the use of a standard etchant, which was 35% phosphoric acid with H$_2$O rinse, and a standard primer which was 13.3% Copolymer/39.8% HEMA/46.9% H$_2$O. The results of these bond strength evaluations are set forth in Table II.

TABLE II

| TREATMENT COMPOSITION | SHEAR BOND STRENGTH kg/cm$^2$ |
|---|---|
| 3% SBS$^1$ in water | 75 ± 17 |
| 6% SBS in 89% EtOH/5% H$_2$O | 81 ± 19 |
| 9% SBS in 83% EtOH/8% H$_2$O | 91 ± 26 |
| 3% SBS in EtOH | 52 ± 24 |
| 1% SBS in EtOH | 31 ± 19 |
| 3.5% Sodium Meta Bisulfite/H$_2$O | 0 |
| 4.5% Sodium Thio Sulfate/H$_2$O | 1 ± 3 |
| 2.3% Sodium Sulfite/H$_2$O | 0 |
| 3.6% DHEPT$^2$/EtOH | 2 ± 4 |
| 3.0% DMAPE$^3$/EtOH | 7 ± 8 |
| 3% DMAPE/Acetone | 8 ± 8 |
| 3.6% DHEPT/Acetone | 0 |

$^1$sodium benzenesulfinate
$^2$N,N-bis-(2-hydroxyethyl)-p-toluidine
$^3$4-(dimethylamino)phenethyl alcohol This experiment shows that the adhesion of amalgam to dentin was significantly higher for treatment solutions that contained an aromatic sulfinate salt, as compared to other electron donor compounds.

EXAMPLE 3

The effect of selection of primer was evaluated by the use of various primers with a standard acid etchant, which was a 35% phosphoric acid followed by water rinse, together with a standard treatment composition, which was 3% sodium benzenesulfinate in ethanol. The results of these bond strength evaluations are reported in Table III.

TABLE III

| PRIMER | SHEAR ADHESIVE BOND STRENGTH (kg/cm$^2$) |
|---|---|
| 13.3% Copolymer/39.8% HEMA/46.9% H$_2$O | 57 ± 14 |
| 7% MDP$^1$/42.7% HEMA/50.3% H$_2$O | 121 ± 14 |
| 2.4% phenol/44.9% HEMA/52.9% H$_2$O | 60 ± 30 |
| 0.45% H$_2$O/44.8% HEMA/52.8% H$_2$O | 57 ± 52 |
| 1.5% acetic acid/45.2% HEMA/53.3% H$_2$O | 53 ± 36 |
| 2.9% maleic acid/44.6% HEMA/52.5% H$_2$O | 52 ± 14 |
| 2.3% oxalic acid/44.9% HEMA/52.9% H$_2$O | 40 ± 15 |
| 1.3% nitric acid/45.3% HEMA/53.4% H$_2$O | 37 ± 23 |
| 0.92% HCl/41.7% HEMA/49.1% H$_2$O | 41 ± 27 |
| 2.5% sulfuric acid/44.8% HEMA/52.8% H$_2$O | 41 ± 33 |
| 1% Copolymer/41.3% H$_2$O/48.7% HEMA | 59 ± 31 |
| 13% Copolymer/H$_2$O | 40 ± 11 |
| 13% Copolymer/EtOH | 29 ± 10 |
| 13% Copolymer/43.5% H$_2$O/43.5% EtOH | 56 ± 32 |
| 7% MDP/13% Copolymer/79.6% H$_2$O | 25 ± 16 |
| 100% TEGDMA | 59 ± 28 |
| 50% Copolymer/23.0% HEMA/27.1% H$_2$O | 19 ± 16 |
| 13% Copolymer/39.8% HEMA/46.9% EtOH | 0 |
| No Primer | 0 |
| 100% HEMA | 21 ± 12 |
| 7.1% MDP/92.9% TEGDMA | 36 ± 28 |
| 1% MDP/99% TEGDMA | 30 ± 35 |

$^1$methacryloxydecyl phosphate

This example shows that significant adhesion of amalgam to dentin is possible through use of a primer using the presently described method.

EXAMPLE 4

The shear bond strength of a high copper admixed alloy amalgam (Disperalloy™ amalgam) and a high copper unicompositional amalgam (Tytin™ amalgam) to dentin was evaluated using an experimental system of the present invention (etchant-35% phosphoric acid with water rinse, treatment composition 3% sodium benzenesulfinate/ethanol, primer-13.3% Copolymer/39.8% HEMA/46.9% water). This system was compared to a commercially available dental adhesive system following the bond strength protocol as defined above.

| SHEAR BOND TO DENTIN | | |
| --- | --- | --- |
| Type of Amalgam | Exptl System (kg/cm$^2$) | All-Bond 2 |
| Tytin | 111 ± 34 | 67 ± 22 |
| Dispersalloy | 57 ± 32 | 32 ± 16 |

The system of the present invention achieved higher shear bond strengths than the commercially available dental adhesive. Also, the high copper unicompositional alloy amalgam exhibited higher bond strength than the high copper admixed alloy amalgam to the substrate.

EXAMPLE 5

The shear bond strength of a high copper admixed alloy amalgam (Disperalloy™ amalgam) and a high copper admixed alloy amalgam (Tytin™ amalgam) to enamel was evaluated using an experimental system of the present invention (etchant-35% phosphoric acid with water rinse, treatment composition 3% sodium benzenesulfinate/ethanol, primer-13.3% Copolymer/39.8% HEMA/46.9% water). This system was compared to a commercially available dental adhesive system following the bond strength protocol as defined above.

| SHEAR BOND TO ENAMEL | | |
| --- | --- | --- |
| Type of Amalgam | Exptl System | All-Bond 2 |
| Tytin | 142 ± 35 | 120 ± 18 |
| Dispersalloy | 83 ± 33 | 90 ± 16 |

The system of the present invention achieved higher shear bond strengths than the commercially available dental adhesive when bonding high copper unicompositional alloy amalgam to enamel. Both systems achieved about the same shear bond strength to enamel for the high copper admixed amalgam.

EXAMPLE 6

The shear bond strength of a high copper admixed alloy amalgam (Disperalloy™ amalgam) and a high copper unicompositional amalgam (Tytin™ amalgam) to set Disperalloy™ amalgam was evaluated using an experimental system of the present invention (etchant-35% phosphoric acid with water rinse, treatment composition 3% sodium benzenesulfinate/ethanol, primer-13.3% Copolymer/39.8% HEMA/46.9% water). This system was compared to a commercially available dental adhesive system following the bond strength protocol as defined above.

| SHEAR BOND TO AMALGAM | | |
| --- | --- | --- |
| Type of Amalgam | Exptl System | All-Bond 2 |
| Tytin | 70 ± 21 | 120 ± 48 |
| Dispersalloy | 26 ± 20 | 71 ± 29 |

Both the experimental system and the commerically available dental adhesive system bonded to set amalgam, with higher bond strengths being achieved by the commercially available product only for this dental surface category. The All-Bond 2 product requires multiple applications of a primer that must be mixed in the dental office. The manufacturer recommends light curing the primer after multiple primer coats have been applied, a step not required in the inventive sytem.

EXAMPLE 7

The shear bond strength of a high copper admixed alloy amalgam (Disperalloy™ amalgam) to various metals was evaluated using an experimental system of the present invention (etchant-35% phosphoric acid with water rinse, treatment composition 3% sodium benzenesulfinate/ethanol, primer-13.3% Copolymer/39.8% HEMA/46.9% water).

| METAL Adherend | SHEAR ADHESIVE BOND STRENGTH (kg/cm$^2$) |
| --- | --- |
| Non-precious | 117 ± 41 |
| 1.8% Beryllum, 4–6% molybdenum, 74–78% Nickel, 12–15% Chromium | |
| Semi-precious | 38 ± 23 |
| 80% Palladium, 1.5% Silver, 2–5% Gold | |
| Precious | 40 ± 21 |
| 62% Gold, 9% Copper, 25% Silver, 3% Palladium | |

This example shows that systems of the present invention achieve excellent bond strength for bonding amalgam to various metals.

What is claimed:

1. A method for adhering amalgam to a dental surface comprising the steps of
   a) etching said dental surface with acid;
   b) applying a treatment composition comprising an aromatic sulfinate salt to said etched dental surface, thereby providing a treated dental surface;
   c) applying a priming solution containing a film-former to said treated dental surface, thereby providing a primed dental surface;
   d) applying a chemically curable dental adhesive to said primed dental surface, thereby providing an adhesive-coated dental surface, said chemically curable adhesive comprising an oxidizing agent and a reducing agent, said oxidizing agent being present in an amount sufficient to interact with said aromatic sulfinate salt to achieve higher adhesion to the dental surface than a like method not comprising an aromatic sulfinate salt in the treatment composition; and
   e) applying amalgam to said adhesive-coated dental surface.

2. The method of claim 1, wherein said dental surface is hard tissue.

3. The method of claim 2, wherein said hard tissue is dentin.

4. The method of claim 1, wherein said dental surface is enamel.

5. The method of claim 1, wherein said dental surface is metal.

6. The method of claim 1, wherein said dental surface is set amalgam.

7. The method of claim 1, wherein said sulfinate salt is represented by the general formula

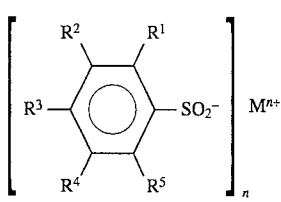

wherein $R^1$, $R^2$, $R^3$, $R^4$ and $R^5$ are independently selected from the group consisting of hydrogen, fluoro, chloro, bromo, iodo, methyl, ethyl, 2-chloroethyl, 2-bromo-2-chloroethyl, propyl, isopropyl, per-fluoropropyl, allyl, butyl, isobutyl, sec-butyl, tert-butyl, pentyl, isopentyl, neopentyl, tert-pentyl, cyclohexyl, phenyl and 4-bromophenyl, and Mn+ is a cation with mono-valency to 4-valency that can, as a counter ion for sulfinic acid anion, form the sulfinate.

8. The method of claim 1, wherein said treatment composition comprises sodium benzenesulfinate.

9. The method of claim 1, wherein said treatment composition comprises water.

10. The method of claim 1, wherein said treatment composition comprises sodium toluenesulfinate.

11. The method of claim 1, wherein said priming solution comprises an acid having a pKa of less than about 10.

12. The method of claim 1, wherein said priming solution comprises HEMA.

13. The method of claim 1, wherein said priming solution comprises polyalkenoic acid copolymer.

14. The method of claim 1, wherein said chemically curable dental adhesive comprises benzoyl peroxide as an oxidizing agent and N,N-bis-(2-hydroxyethyl)-p-toluidine as a reducing agent.

15. The method of claim 1, wherein said chemically curable dental adhesive contains at least about 0.75 weight percent of benzoyl peroxide and N,N-bis-(2-hydroxyethyl)-p-toluidine combined, and the ratio of weight percentages of N,N-bis-(2-hydroxyethyl)-p-toluidine to benzoyl peroxide is greater than 0.05 but less than 1.50.

16. The method of claim 1, wherein said chemically curable dental adhesive contains at least about 1 weight percent of benzoyl peroxide and N,N-bis-(2-hydroxyethyl)-p-toluidine combined, and the ratio of weight percentages of N,N-bis-(2-hydroxyethyl)-p-toluidine to benzoyl peroxide is greater than 0.10 but less than 1.20.

17. The method of claim 1, wherein said chemically curable dental adhesive comprises 2-hydroxyethyl methacrylate and Bisphenol A diglycidyl methacrylate.

18. The method of claim 1, wherein said amalgam is a high copper unicompositional amalgam.

19. The method of claim 1, wherein said adhered amalgam exhibits Shear Adhesive Strength to dentin greater than about 10 kg/cm$^2$ when said amalgam is a high copper admixed amalgam.

20. The method of claim 1, wherein said adhered amalgam exhibits a Shear Adhesive Strength to dentin greater than about 30 kg/cm$^2$ when said amalgam is a high copper admixed amalgam.

* * * * *